United States Patent
Mukhopadhyay et al.

(10) Patent No.: US 6,809,177 B1
(45) Date of Patent: Oct. 26, 2004

(54) PROCESS FOR THE CONVERSION OF ECHINOCANDIN CLASS OF PEPTIDES TO THEIR C4-HOMOTYROSINE MONODEOXY ANALOGUES

(75) Inventors: Triptikumar Mukhopadhyay, Mumbai (IN); Kenia Jayvanti, Mumbai (IN); Erra Koteswara Satya Vijaya Kumar, Mumbai (IN)

(73) Assignee: Aventis Pharma Deutschland GmbH., Frankfurt (DE)

( * ) Notice: Subject to any disclaimer, the term of this patent is extended or adjusted under 35 U.S.C. 154(b) by 0 days.

(21) Appl. No.: 09/673,836

(22) PCT Filed: Apr. 22, 1999

(86) PCT No.: PCT/EP99/02715
§ 371 (c)(1),
(2), (4) Date: Mar. 29, 2001

(87) PCT Pub. No.: WO99/55727
PCT Pub. Date: Nov. 4, 1999

(30) Foreign Application Priority Data

Apr. 23, 1998 (EP) ............................................. 98107397

(51) Int. Cl.[7] ........................ A61K 38/12; A61K 38/00; C07K 7/00; C12P 21/04
(52) U.S. Cl. ........................ 530/317; 530/318; 530/345; 530/402; 530/406; 435/71.3; 930/190; 930/270; 930/DIG. 546; 514/9; 514/11
(58) Field of Search ................................ 530/317, 318, 530/345, 402, 406; 435/71.3; 930/190, 270, DIG. 546; 514/11, 9

(56) References Cited
U.S. PATENT DOCUMENTS 5,159,059 A  * 10/1992 Balkovec et al. ........... 530/317
5,677,423 A  * 10/1997 Rodriguez .................. 530/345
5,684,128 A  * 11/1997 Balkovec et al. ............ 530/317

FOREIGN PATENT DOCUMENTS

| EP | 0 459 564 A2 | 12/1991 |
|---|---|---|
| EP | 0 535 959 A1 | 4/1993 |
| EP | 0 535 968 A1 | 4/1993 |
| EP | 0 644 199 A1 | 3/1995 |
| WO | 96/08266 | 3/1996 |

OTHER PUBLICATIONS

Mukhopadhyay et al., The Journal of Antiniotics, vol. 40, No. 3, pp. 281–289, Mar. 1987.*

Mukhopadhyayet al., The Journal of Antibiotics, vol. 45, No. 5, pp. 618–623, May 1992.*

Balkovec et al., "Reduction Studies of Antifungal Echinocandin Lipopeptides. One Step Conversion of Echinocandin B to Echinocandin C.," *Tetrahedron Letters*, 33(32):4529–4532 (1992).

* cited by examiner

*Primary Examiner*—Robert A. Wax
*Assistant Examiner*—Abdel A. Mohamed
(74) *Attorney, Agent, or Firm*—Irving Newman

(57) ABSTRACT

The invention relates to a process for the conversion of echinocandin class of peptides to their C4-homotyrosine monodeoxy analogues, particularly mulundocandin to deoxymulundocandin, which consists of a single step selective reduction of C4-htyr (homotyrosine) hydroxyl group of echinocandins to their monodeoxy analogues under neutral conditions without prior protection/deprotection of the equally facile C5-Orn (ornithine) hydroxyl group and purification of the monodeoxy compound from the crude reaction mixture.

3 Claims, 2 Drawing Sheets

Figure 1:
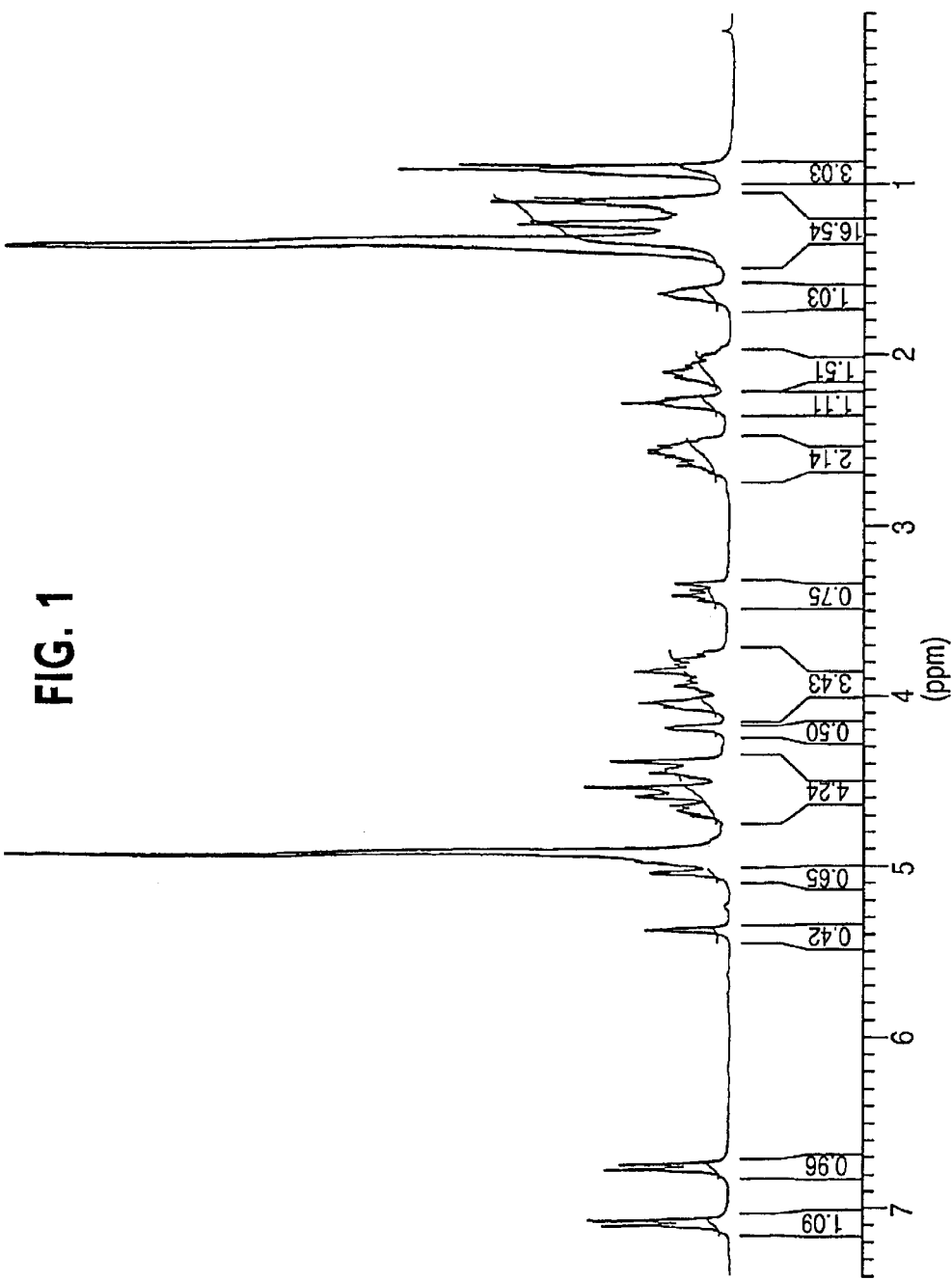

PROCESS FOR THE CONVERSION OF ECHINOCANDIN CLASS OF PEPTIDES TO THEIR C4-HOMOTYROSINE MONODEOXY ANALOGUES

FIELD OF THE INVENTION

This invention relates to a process for the conversion of echinocandin class of peptides of the formula I

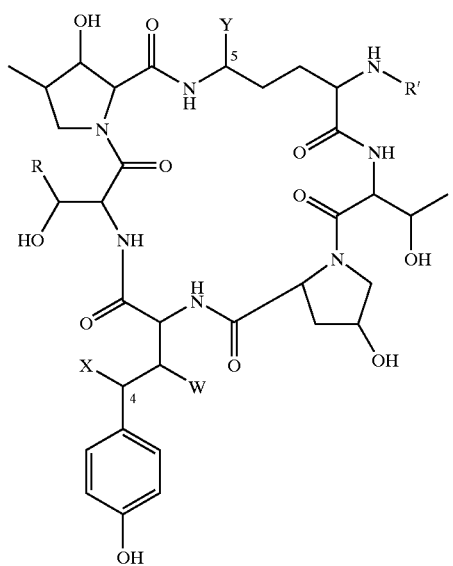

(I)

wherein W, X, Y, Z, R and R' are as defined herein below:

| | W | X | Y | Z | R | R' |
|---|---|---|---|---|---|---|
| 1. Echinocandin B | OH | OH | OH | OH | $CH_3$ | Linoleoyl |
| 2. Pneumocandin $A_0$ | OH | OH | OH | OH | $CH_2$—$CONH_2$ | 10,12-Dimethyl-myristoyl |
| 3. Pneumocandin $A_1$ | H | OH | OH | OH | $CH_2$—$CONH_2$ | 10,12-Dimethyl-myristoyl |
| 4. Pneumocandin $A_2$ | OH | OH | H | H | $CH_2$—$CONH_2$ | 10,12-Dimethyl-myristoyl |
| 5. Pneumocandin $B_0$ | OH | OH | OH | OH | $CH_2$—$CONH_2$ | 10,12-Dimethyl-myristoyl |
| 6. Pneumocandin $B_2$ | OH | OH | H | H | $CH_2$—$CONH_2$ | 10,12-Dimethyl-myristoyl |
| 7. Pneumocandin $C_0$ | OH | OH | OH | OH | $CH_2$—$CONH_2$ | 10,12-Dimethyl-myristoyl |
| 8. Mulundocandin | OH | OH | OH | OH | H | 12-Methyl-tetradecnoyl | to their C4-homotyrosine monodeoxy analogues of the formula I wherein W, Y, Z, R and R' are as defined herein below:

| | W | X | Y | Z | R | R' |
|---|---|---|---|---|---|---|
| 1. Deoxyechinocandin B (Echinocandin C) | OH | H | OH | OH | $CH_3$ | Linoleoyl |
| 2. Deoxypneumocandin $A_0$ | OH | H | OH | OH | $CH_2$—CO—$NH_2$ | 10,12-Dimethyl-myristoyl |
| 3. Deoxypneumocandin $A_1$ | H | H | OH | OH | $CH_2$—$CONH_2$ | 10,12-Dimethyl-myristoyl |
| 4. Deoxypneumocandin $A_2$ | OH | H | H | H | $CH_2$—$CONH_2$ | 10,12-Dimethyl-myristoyl |
| 5. Deoxypneumocandin $B_0$ | OH | H | OH | OH | $CH_2$—$CONH_2$ | 10,12-Dimethyl-myristoyl |
| 6. Deoxypneumocandin $B_2$ | OH | H | H | H | $CH_2$—$CONH_2$ | 10,12-Dimethyl-myristoyl |
| 7. Deoxypneumocandin $C_0$ | OH | H | OH | OH | $CH_2$—$CONH_2$ | 10,12-Dimethyl-myristoyl |
| 8. Deoxymulundocandin | OH | H | OH | OH | H | 12-Methyl tetradecanoyl, | particularly to a process for the conversion of mulundocandin (compound of the formula II)

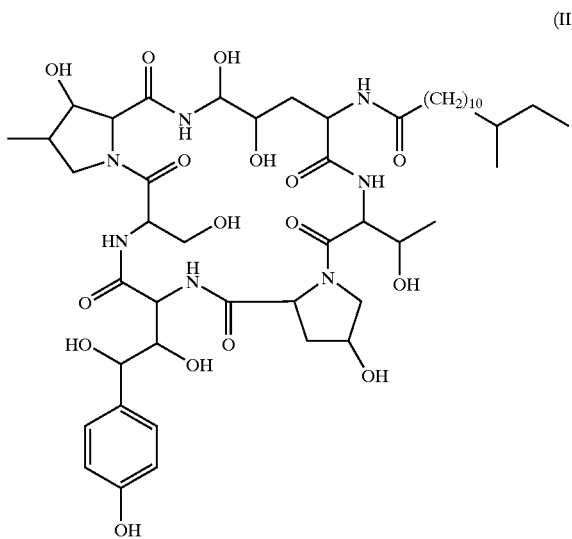

to deoxymulundocandin (compound of the formula III)

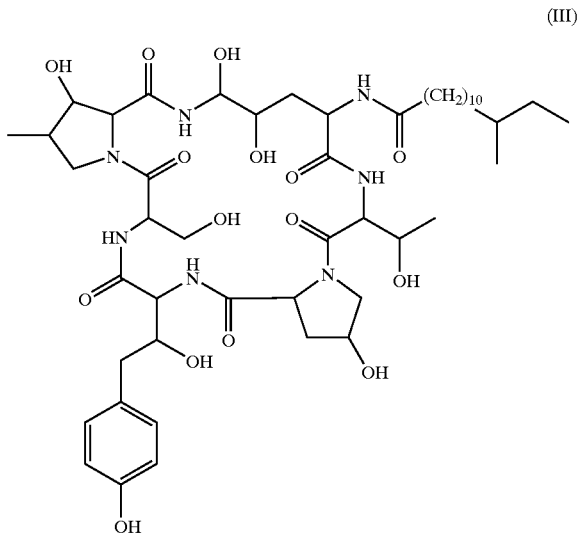

BACKGROUND OF THE INVENTION 1,3-β-glucan synthesis inhibitors are effective antifungal agents *Candida albicans* and also *Pneumocystis carini,* an opportunistic organism responsible for an often fatal pneumonitis among HIV patients and other immunocompromised hosts. Of all the structural classes of 1,3-β-glucan synthesis inhibitors, only the echinocandins received considerable attention [Ref: J. Med. Chem. 35, 198–200 (1992)]. Echinocandin class of peptides are cyclic hexapeptides having a lipophilic side chain.

Several methods for the conversion of echinocandins to the corresponding deoxy analogues under acidic conditions have been reported [Ref: Tetrahedron Letts., 33, 4529–4532 (1992); U.S. patent application Ser. No. 222,157 dated Apr. 4, 1994]. The above methods involve selective reduction of C4-htyr (homotyrosine) hydroxyl group of echinocandins to their monodeoxy analogues with prior protection/deprotection of the equally facile C5-Orn (ornithine) hydroxyl group.

Mulundocandin [J.Antibiotics, 40, 275–280 and 281–289 (1987)] and deoxymulundocandin [Indian patent No. IN I69830 ; J.Antibiotics. 45, 618–623 (1992)] having antifungal properties were isolated from *Aspergillus sydowii* (Bainier and Sartory) Thom and Church var. Nov. Mulundensis Roy (culture no.HIL Y-30462). Deoxymulundocandin was found to possess better antifungal activity than mulundocandin. However, the production of deoxymulundocandin during the fermentation was 200 times less than that of mulundocandin.

We have found out by extensive research and experimentation that echinocandin class of peptides of the formula I may be converted to the corresponding C4-htyr monodeoxy analogues, particularly mulundocandin to deoxymulundocandin under neutral conditions. Accordingly, the object of the present invention is to provide a process for the conversion of echinocandin class of peptides of the formula I to the corresponding C4-homotyrosin monodeoxy analogues, particularly mulundocandin (compound of formula II) to deoxymulundocandin (compound of formula III).

SUMMARY OF THE INVENTION

According to the invention, there is provided a process for the conversion of echinocandin class of peptides of the formula I

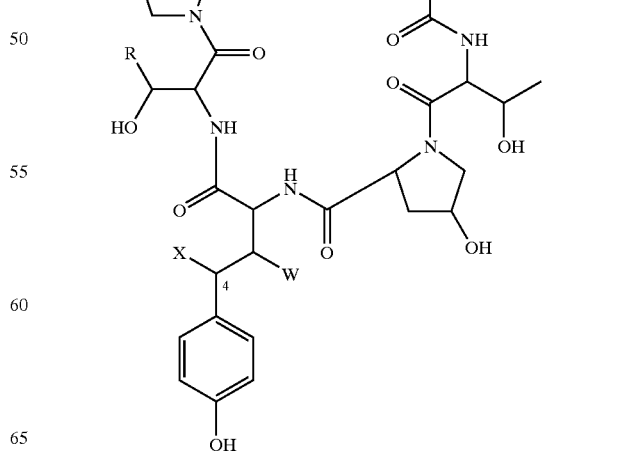

wherein W, X, Y, Z, R and R' are as defined herein below:

|   | W | X | Y | Z | R | R' |
|---|---|---|---|---|---|---|
| 1. Echinocandin B | OH | OH | OH | OH | $CH_3$ | Linoleoyl |
| 2. Pneumocandin $A_0$ | OH | OH | OH | OH | $CH_2$—CO—$NH_2$ | 10,12-Dimethyl-myristoyl |
| 3. Pneumocandin $A_1$ | H | OH | OH | OH | $CH_2$—CO—$NH_2$ | 10,12-Dimethyl-myristoyl |
| 4. Pneumocandin $A_2$ | OH | OH | H | H | $CH_2$—CO—$NH_2$ | 10,12-Dimethyl-myristoyl |
| 5. Pneumocandin $B_0$ | OH | OH | OH | OH | $CH_2$—CO—$NH_2$ | 10,12-Dimethyl-myristoyl |
| 6. Pneumocandin $B_2$ | OH | OH | H | H | $CH_2$—CO—$NH_2$ | 10,12-Dimethyl-myristoyl |
| 7. Pneumocandin $C_0$ | OH | OH | OH | OH | $CH_2$—CO—$NH_2$ | 10,12-Dimethyl-myristoyl |
| 8. Mulundocandin | OH | OH | OH | OH | H | 12-Methyl-tetradecanoyl | to the C4-homotyrosine monodeoxy analogues of the formula I, wherein W, X, Y, Z, R and R' are as defined herein below:

|   | W | X | Y | Z | R | R' |
|---|---|---|---|---|---|---|
| 1. Deoxyechinocandin B (Echinocandin C) | OH | H | OH | OH | $CH_3$ | Linoleoyl |
| 2. Deoxypneumocandin $A_0$ | OH | H | OH | OH | $CH_2$—CO—$NH_2$ | 10,12-Dimethyl-myristoyl |
| 3. Deoxypneumocandin $A_1$ | H | H | OH | OH | $CH_2$—CO—$NH_2$ | 10,12-Dimethyl-myristoyl |
| 4. Deoxypneumocandin $A_2$ | OH | H | H | H | $CH_2$—CO—$NH_2$ | 10,12-Dimethyl-myristoyl |
| 5. Deoxypneumocandin $B_0$ | OH | H | OH | OH | $CH_2$—CO—$NH_2$ | 10,12-Dimethyl-myristoyl |
| 6. Deoxypneumocandin $B_2$ | OH | H | H | H | $CH_2$—CO—$NH_2$ | 10,12-Dimethyl-myristoyl |
| 7. Deoxypneumocandin $C_0$ | OH | H | OH | OH | $CH_2$—CO—$NH_2$ | 10,12-Dimethyl-myristoyl |
| 8. Deoxymulundocandin | OH | H | OH | OH | H | 12-Methyl tetradecanoyl | particularly to a Process for the conversion of Mulundocandin (compound of the formula II to deoxymulundocandin (compound of the formula III)

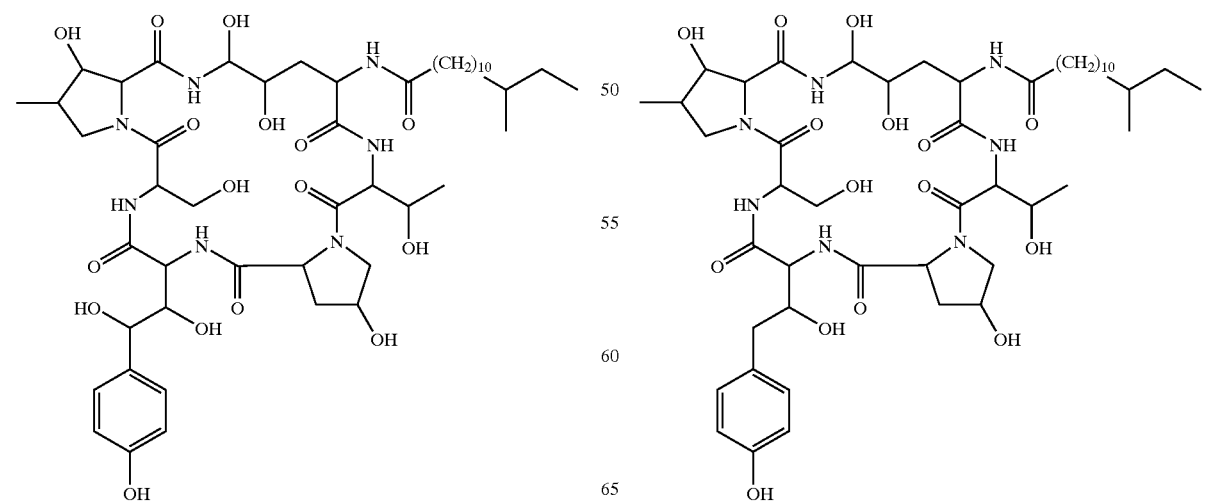

which consists of a single step selective reduction of C4-htyr (homotyrosine) hydroxyl group of echinocandins to their monodeoxy analogues particularly under neutral conditions without prior protection, deprotection of the equally facile C5-Orn (ornithe) hydroxyl group and purification of the monodeoxy compound from the crude reaction mixture.

DETAILED DESCRIPTION OF THE INVENTION

The conversion of echinocandins to their monodeoxy analogues by selective reduction at C4-htyr may be effected by hydrogenolysis with Raney nickel in solvents such as methanol, ethanol or dioxane at pH 3–9. Preferably, the selective reduction is carried out by hydrogenolysis with Raney nickel in ethanol at pH 7 and room temperature in the ratio of 6.8 ml Raney nickel per millimole of mulundocandin.

The monodeoxy compounds of the invention may, for example, be purified from the crude reaction mixture as follows:

By fractionation using normal phase chromatography (using alumina or silica gel as stationary phase and eluents such as petroleum ether, ethyl acetate, dichloromethane, chloroform, methanol or combination thereof), reverse phase chromatography (using reverse silica gel like dimethyloctadecylsilylsilica gel, also called RP-18 or dimethyloctylsilsilica gel also called RP8 as stationary phase and eluents such as water, buffers such as phosphate, acetate, citrate (pH 2–8) and organic solvents such as methanol, acetonitrile, acetone, tetrahydrofuran or combination of solvents). gel permeation chromatography—using resins such as SEPHADEX LH-20® (Pharmacia Chemical Industries, Sweden), TSKgel Toyopearl HW (TosoHaas, Tosoh Corporation, Japan), in solvents such as methanol, chloroform or ethyl acetate or their combination or SEPHADEX G-10® and SEPHADEX G-25® in water; or by counter-current chromatography using a biphasic eluent system made up of two ore more solvents such as water, methanol, ethanol, iso-propanol, n-propanol, tetrahydrofuran, acetone, acetonitrile, methylene chloride, chloroform, ethylacetate, petroleum ether, benzene and toluene. These techniques may be used repeatedly or a combination of the different techniques may used. Counter-current chromatography (liquid-liquid chromatography) using a biphasic eluent system ITO coil is preferred for purification of the compounds of the invention.

The following experimental example is illustrative of the present invention but not limitative of the scope thereof.

Example 1

Mulundocandin (220 mg, 2.2 mM) in ethanol (8 ml)) was stirred with 15 ml of W-2 Raney nickel (pH 7) in ethanol (30 ml) for 3 hours at room temperature. After standing for 15 minutes the supernatent solution was decanted and Raney nickel washed with 3×30 ml. ethanol with stirring and filtered. Combined ethanolic solutions were concentrated by distillation under a reduced pressure of 60–70 mm/Hg at 35° C. to obtain 160 mg (75%) of crude deoxymulundocandin as a slightly green solid.

The crude product was purified by liquid-liquid chromatography on ITO coil using upper layer of $CH_2Cl_2$:MeOH:n-PrOH:$H_2O$ as the stationary phase and the lower layer as the mobile phase in an ascending mode. The coils (15+25+215 ml) were connected in series and a flow rate of 0.6 ml/min. at a piston stroke of 60 and pressure 0.5 bars was maintained. The purification of deoxymulundocandin was monitored both by bioactivity against *Candida albicans* and *Aspergillus niger* and by analytical High Pressure Liquid Chromatography (HPLC) [column: (10×0.4 cm+3×0.4 cm) ODS-Hypersil, 10µ; mobile phase: 50:50 $CH_3CN$:$H_2O$; flow rate:1 ml/min; Wavelength; 220 nm.) The fractions (4.5 ml each) containing deoxymulundocandin were combined, concentrated by distillation under a reduced presssure of 60–70 mm/Hg at 35° C. and lyophilized to yield pure deoxymulundocandin [65 mg (30% yield)]. Also recovered during the above purification of deoxymulundocandin was unreacted mulundocandin in 10% yield.

The semi-synthetic deoxymulundocandin was identical in all respects to the naturally isolated compound and the physico-chemical data is given in Table 1.

TABLE 1

Figure 2:
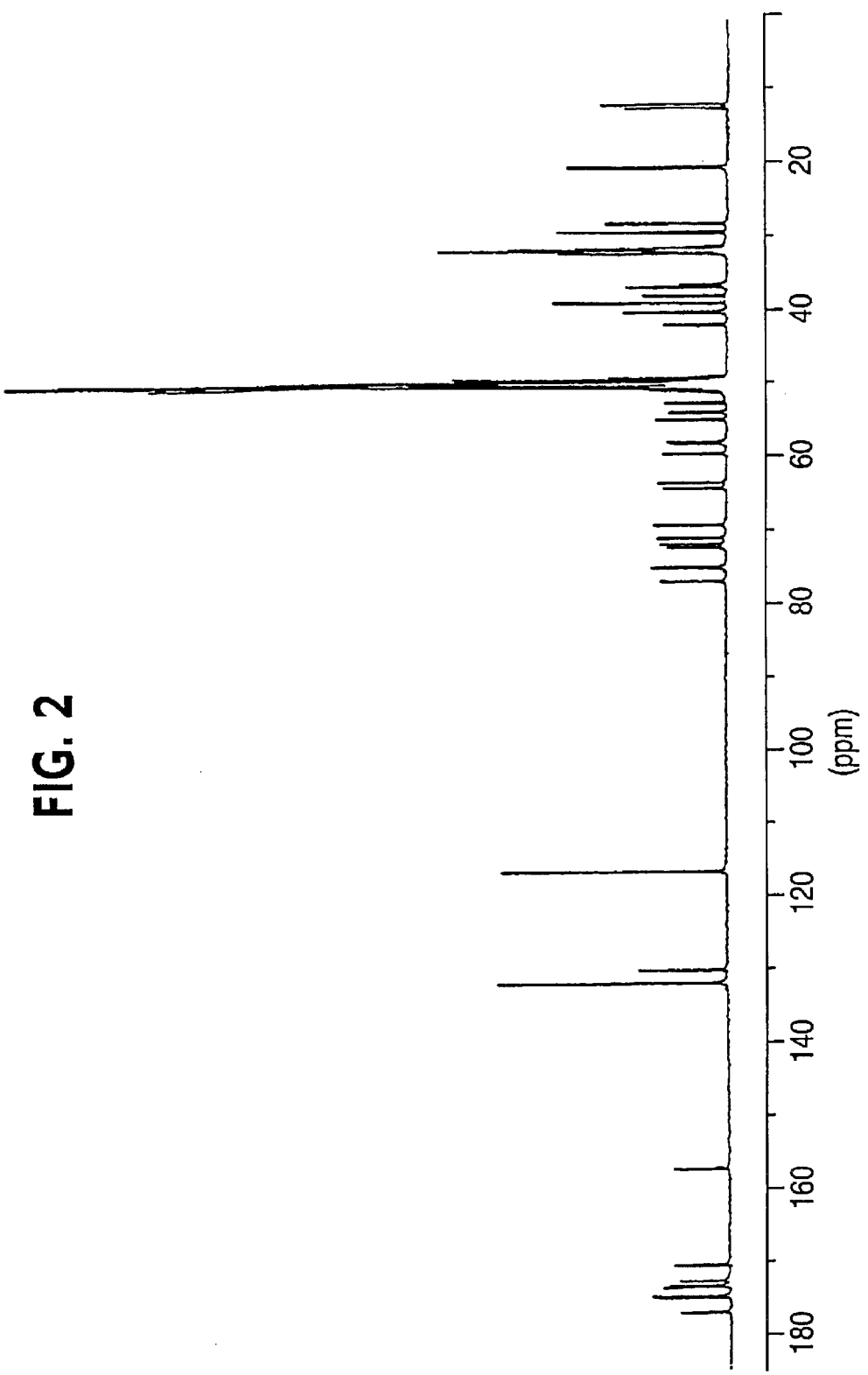

| | |
|---|---|
| Appearance | White powder |
| Melting point | 170–172° C. |
| $[\alpha]_D$ | −36.6° (c 0.25, MeOH) |
| HPLC RT | 4.42 min |
| FAB-MS (Fast Atom Bombardment mass) | 1014.7 $(M + Na)^+$ |
| $^1H$ NMR (300 MHz, $CD_3OD$) | FIG. 1 of the accompanying drawings |
| $^{13}C$ NMR (75 MHz, $CD_3OD$) | FIG. 2 of the accompanying drawings |

What is claimed is:

1. A process for converting mulundocandin of formula I:

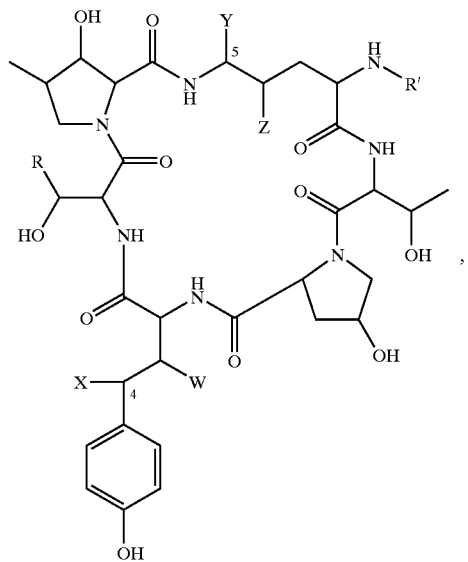

wherein each of W, x, Y and Z is OH, R is H and R' is 12-methyl-tetradecanoyl, to deoxymulundocandin, a compound of formula I wherein W, Y and Z are each OH, X and R are each H and R' is 12-methyl-tetradecanoyl, this process comprising reducing the C4-htyr (homotyrosine) hydroxyl group of said mulundocandin by mixing said mulundocandin with Raney Nickel in a solvent selected from the group consisting of methanol, ethanol and dioxane at a pH of 3–7 without protecting and then deprotecting the C5-orn (ornithine) hydroxyl group, and then purifying the resulting deoxymulundocandin from the crude reaction mixture.

2. A process as claimed in claim 1, wherein said reducing of the C4-htyr (homotyrosine) hydroxyl group is carried out by hydrogenolysis with Raney nickel in ethanol at pH 7 and at room temperature.

3. A process as claimed in claim 2, wherein the hydrogenolysis is carried out in the ratio of 6.8 ml of Raney nickel per millimole of mulundocandin.

* * * * *